United States Patent [19]

Nelson

[11] 4,453,018

[45] Jun. 5, 1984

[54] PROCESS FOR THE ALKYLATION OF PHENOLIC COMPOUNDS WITH ALKYL SULFITES

[75] Inventor: Randall B. Nelson, Shelton, Wash.

[73] Assignee: International Telephone and Telegraph Corporation, New York, N.Y.

[21] Appl. No.: 364,327

[22] Filed: Apr. 1, 1982

[51] Int. Cl.³ .................... C07C 41/16; C07C 45/61
[52] U.S. Cl. .................... 568/433; 562/475; 564/223; 568/312; 568/630; 568/648; 568/655
[58] Field of Search ............. 568/433, 648, 312, 655, 568/630; 564/223; 562/475

[56] References Cited

U.S. PATENT DOCUMENTS 3,867,458  2/1975  Imai et al. ........................ 568/433

OTHER PUBLICATIONS

Voss et al., Justus Liebig Ann., vol. 485, (1931), pp. 258–283.
Hara et al., Bulletin of the Chemical Society of Japan, vol. 49, (4), (1976), pp. 1126–1129.

*Primary Examiner*—Bernard Helfin
*Attorney, Agent, or Firm*—James B. Raden; Harold J. Holt

[57] ABSTRACT

An alkylated phenolic ether is prepared by reacting in the absence of a protic solvent a phenolic compound containing an unreacted phenolic hydroxy group with an alkyl sulfite of the formula $(RO)_2SO$ in which R is a one to four carbon alkyl group, the reaction occurring in one step and without the intermediate preparation of a phenolate.

9 Claims, No Drawings

PROCESS FOR THE ALKYLATION OF PHENOLIC COMPOUNDS WITH ALKYL SULFITES

This invention relates to a process for the preparation of an alkylated phenolic ether from the corresponding phenolic compound.

It is well known that phenols, particularly lignin derived phenols, may be generally alkylated by the use of alkyl sulfates, alkyl halides or alkyl sulfonates. A typical example of such a reaction is shown in *Organic Syntheses,* Collective Vol. II, page 619, 1943, in which veratraldehyde is prepared from vanillin, a lignin derived chemical. The process there shown is a two-step reaction involving the preparation of an intermediate sodium salt or phenolate with an alkali hydroxide, or other strong base, and water as a solvent and the subsequent alkylation of the phenolate with dimethyl sulfate to produce the alkylated phenol. This process is similar to those employed in the chemical industry for the production of veratraldehyde from vanillin.

These processes are hazardous in that the alkyl sulfates, alkyl halides, and alkyl sulfonates are toxic and present exposure problems due to their volatility. Less hazardous alkylating agents are known but they have not been commercially used because they tend to hydrolyze during the alkylation reaction resulting in relatively poor yields. One such reaction is shown, for example, in W. Voss and E. Blanke, *Ann. der Chemie,* 485, 258 (1931) where an alkyl sulfite is used for the conversion of phenol to anisole by the two-step sodium phenolate reaction. Alkyl sulfites have also been disclosed as useful in the O-alkylation of stabilized enolates. See, for example, Y. Hara and M. Matsuda, *Bull. Chem. Soc.* (Japan), 49, 1126 (1976).

It is a primary object of the present invention to provide an effective process for the production of phenolic ethers by the alkylation of phenols which does not require the use of hazardous alkylating agents.

It is an additional object of the invention to provide such an alkylation process which is relatively simple and involves mild reaction conditions.

The foregoing and other objects of the invention are achieved in a process for the preparation of an alkylated phenolic ether which comprises reacting in the absence of a protic solvent a phenolic compound containing an unreacted phenolic hydroxy group with an alkyl sulfite of the formula $(RO)_2SO$ in which R is a one to four carbon alkyl group until an alkylated phenol is produced, the reaction occuring in one step and without the intermediate preparation of a phenolate.

The present process may be carried out as a melt phase reaction in the absence of a solvent or, alternatively, may be carried out in the presence of an aprotic solvent, preferably a dipolar aprotic solvent, together with a weak base. The melt phase alkylation reaction is carried out at a temperature of at least the melting point of the phenol, preferably in the presence of a small amount of a base catalyst. The melt phase reaction is the subject of my copending application Ser. No. 364,325, filed of even date herewith. Further and more detailed description of the melt phase reaction may be obtained from the foregoing copending application, the disclosure of which is hereby incorporated by reference. If the alkylation reaction is carried out in the presence of an aprotic solvent, from 0.1 to 10 mol percent of a weak base such as a carbonate salt should be used. The carbonate salt may, for example, be sodium, potassium, magnesium or calcium carbonate.

The present process avoids the prior formation of a phenolate and it is carried out in the absence of a protic solvent. Two step phenolic alkylation via the phenolate reaction requires the presence of a protic solvent or at least a protic component in the solvent. Prior phenolic alkylation reactions either introduced a protic solvent, such as water, at the start of the reaction, or insured the formation of a protic solvent during the course of the reaction by the addition of a strong base. In the present process, the reaction is carried out in the melt phase and no solvent is used or, alternatively, the reaction is carried out under anhydrous conditions in the presence of an aprotic solvent. If an aprotic solvent is used, it is used in conjunction with a weak base so that a protic solvent is not formed during the alkylation reaction. For the same reasons, the reaction is carried out under anhydrous conditions to avoid the presence of water, a protic solvent. Suitable examples of dipolar aprotic solvents which may be used in the practice of the invention are dimethylformamide, dimethylacetamide, dimethylsulfoxide and sulfolane.

The starting phenolic compound will normally be a lignin derived mono- or polycyclic phenol. The reaction may generally be represented by the following equation showing the conversion of the phenolic compound into the corresponding ether:

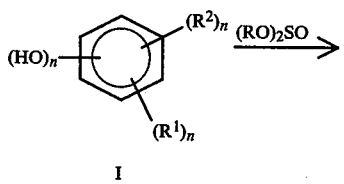

I

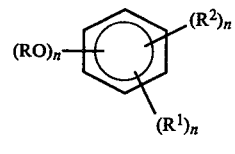

II

In the formulae above, $R^1$ and $R^2$ may be the same or different and are a radical selected from the group consisting of H, OH, alkyl, alkenyl, cycloalkyl, alkoxy, aryl, halogen and a carbonyl radical such as an aldehyde, ketone, ester, amide and acid, at least one of $R^1$ and $R^2$ preferably being $-COR^3$ where $R^3$ is hydrogen, an alkyl, cycloalkyl or aryl radical. R is a one to four carbon atom alkyl group. n is from one to four. Where $R^1$ or $R^2$ is aryl, it may be attached to a single carbon atom of the phenolic nucleus (to form a biphenyl, for example) or it may share two carbon atoms to form a polycyclic phenol (as for example, naphthalene compounds). The orientation of the radicals may be varied in the ortho, meta or para position with respect to the $-OH$ group and with respect to each other.

The alkylating agent is a dialkyl sulfite of the formula $(RO)_2SO$ in which R is one to four carbon alkyl group, preferably a one to four carbon alkyl group such as dimethyl, diethyl, dipropyl or dibutyl sulfite. The alkylating agent need not be added in excess, however an excess is preferable.

In the final alkylated product, the —OH group, or groups, are substituted with the alkyl moiety of the alkylating agent to become the corresponding ether of the starting compound.

Examples of phenolic compounds falling within the above formula I are such monohydric phenols as phenol and o-, m- and p-cresol and guaiacol; phenolic aldehydes such as protocatechualdehyde, vanillin, syringaldehyde, p-hydroxybenzaldehyde and 5-formylvanillin; phenolic ketones such as p-hydroxyacetophenone, acetovanillone, acetosyringone and acetamidophenol; phenolic acids such as vanillic acid, syringic acid and p-hydroxybenzoic acid. The preferred phenolic reactants are those having at least one carbonyl functionality.

A key advantage of the present process is the substantially greater level of safety of the alkyl sulfite alkylating agents as compared with traditional alkylating agents. All alkylating agents are potentially hazardous, but the degree of severity of the sulfites is substantially less than that of the sulfates, halides or sulfonates. Alkyl sulfites are rapidly hydrolyzed to $SO_2$ and the corresponding alcohol by water. $SO_2$ and alcohol are relatively innocuous as compared, for example, to sulfuric acid formed by the hydrolysis of alkyl sulfates.

In a preferred embodiment of the process of the invention utilizing the melt phase reaction, a lignin derived phenol is melted and contacted with an anhydrous alkali carbonate and two to three molar excess of the dialkylsulfite under at least atmospheric pressure. Alternatively, the carbonate may be added before melting is initiated. The dialkylsulfite is added progressively, i.e., incrementally as the reaction progresses, so as to keep the reaction temperature near the initial feed temperature, i.e., about 5° to 10° C. above the melting point of the phenol, until a slight stoiciometric excess (the preferred amount is usually about 1.2 molar equivalents of alkylating agent relative to phenol) of alkylating agent has been added. After addition of alkylating agent, the temperature is maintained for a brief period (i.e., several hours) to insure completion of reaction and then the mixture is cooled to a moderate (e.g., 50° C.) temperature and drowned in water. Total reaction time is normally from 1 to 10 hours. The product can be collected directly or, if an oil, can be extracted into a suitable organic solvent and recovered in a manner familiar to those skilled in the art. Alternatively, the oil itself may be separated from the drowned reaction mixture and purified by one of several known standard methods such as fractional distillation. For many purposes, however, the crude product is of sufficient purity (often 95% assay) for use directly in the intended product.

In a preferred embodiment of the process of the invention utilizing a dipolar aprotic solvent, a lignin derived phenol is dissolved in the anhydrous solvent and contacted with an anhydrous alkali carbonate and two to three molar excess of the dialkyl sulfite under at least atmospheric pressure. Alternatively, the carbonate may be added before dissolution is initiated. The mixture is heated to a suitable temperature (usually near 100° C.) and the dialkylsulfite is added progressively, i.e., incrementally as the reaction progresses, so as to keep the reaction temperature near the initial feed temperature, until a slight stoiciometric excess (the preferred amount is usually about 1.2 molar equivalents of alkylating agent relative to phenol) of alkylating agent has been added. After addition of alkylating agent, the temperature is maintained for a brief period (i.e., several hours) to insure completion of reaction and then the mixture is cooled to a moderate (e.g., 50° C.) temperature and drowned in water. Total reaction time is normally 1 to 10 hours. The product can be collected, extracted and recovered as set forth above for the melt phase reaction.

The following examples illustrates the practice of the invention. Unless otherwise indicated, all parts and percentages are by weight.

EXAMPLE 1

This example illustrates the preparation of 3, 4, 5-trimethoxybenzaldehyde from syringaldehyde.

In a three-neck flask (capacity 100 ml) equipped with a mechanical stirrer and reflux condenser, 10.0 g (0.054 mol) of syringaldehyde and 5.00 g (0.036 mol) of anhydrous potassium carbonate were placed and the mixture was heated under a nitrogen atmosphere to 100° C. To this mixture was added 8.00 ml (0.094 mol) of dimethyl sulfite over about 5 minutes while maintaining the reaction temperature below 125° C. The pasty mixture was maintained at about 100° C. for three hours and then cooled to 25° C. and quenched with 50 ml water. The mixture was extracted with 100 ml of methylene chloride. The extracts were washed with water and concentrated in vacuo to give 4.2 g of 3, 4, 5-trimethoxybenzaldehyde.

EXAMPLE 2

This example illustrates the preparation of p-acetamidoanisole from p-acetamidophenol.

To a three-necked 100 ml flask equipped for reflux and fitted with a mechanical stirrer was added 10 ml (0.12 mol) of dimethyl sulfite, 2.0 g (0.014 mol) of potassium carbonate, and 5.0 g (0.033 mol) of p-acetamidophenol. The mixture was heated to 70° C. for six hours then quenched while hot with 50 ml of water. The solution was made basic with dilute caustic and the organic materials were extracted into methylene chloride. The extracts were concentrated in vacuo to give 2.0 g of p-acetamidoanisole.

EXAMPLE 3

This example illustrates the preparation of veratraldehyde from photocatechualdehyde.

To a three-necked 100 ml flask equipped for reflux and fitted with a mechanical stirrer was added 1.0 g (0.0072 mol) of protocatechualdehyde 1.0 g (0.007 mol) of potassium carbonate, and 4.0 ml (0.047 mol) of dimethyl sulfite. The mixture was heated for four hours then quenched hot with 25 ml of water. The organic material was extracted into methylene chloride and the extracts were washed with 15 ml of 12% caustic solution, 25 ml of water and then concentrated in vacuo to obtain 0.5 g of crude veratraldehyde.

EXAMPLE 4

This example illustrates the preparation of veratric acid methyl ester from vanillic acid.

To a three-necked 100 ml flask equipped for reflux and fitted with a mechanical stirrer is added 1.0 g (0.006 mol) of vanillic acid, 1.0 g (0.007 mol) of potassium carbonate, and 4.0 ml (0.047 mol) of dimethyl sulfite. The mixture was heated to 70° C. for three hours then quenched while hot with 15 ml of water. The organics were extracted into 25 ml of methylene chloride, washed with 15 ml of 12% caustic and then washed with water. The extracts were dried over anhydrous $K_2CO_3$, filtered and concentrated in vacuo to get 0.8 g (68%) veratric acid methyl ester.

EXAMPLE 5

This example illustrates the preparation of methyl p-methoxybenzoate from p-hydroxybenzoic acid.

To a 100 ml three-necked flask equipped for reflux and fitted with a mechanical stirrer was added 2.0 g (0.014 mol) of p-hydroxybenzoic acid, 1.0 g. (0.007 mol) of potassium carbonate, and 5.0 ml (0.059 mol) of dimethyl sulfite. The mixture was heated at 100° C. for four hours and then quenched with 15 ml of water. The organics were taken up with methylene chloride and washed sequentially with 12% caustic solution and water. The extracts were concentrated in vacuo to give 1.28 g of methyl p-methoxybenzoate.

EXAMPLES 6-11

A series of additional reactions were run using melt phase reaction conditions similar to those set forth in the foregoing examples. A slurry of the phenolic substrate was mixed with an optimal quantity of anhydrous potassium carbonate and two to three molar excess of dimethyl sulfite. This mixture was heated to about 80°-100° C. for three to four hours, cooled, quenched with water, and the product extracted into methylene chloride. Prior to analysis by thin layer chromatography, the methylene chloride extracts were washed with a dilute solution of sodium hydroxide to remove any phenolic starting material. The ethereal neutral products of reaction were contrasted with the phenolic starting material and a known standard sample of the expected product, where available. Spectral analysis via infrared spectra was used when a question remained as to product identity. The following products were produced from the following starting phenolic compounds:

| Example | Starting Phenol | Product |
|---|---|---|
| 6 | p-acetamidophenol | p-acetamidoanisole |
| 7 | protocatechualdehyde | veratraldehyde |
| 8 | vanillic acid | veratric acid |
| 9 | syringaldehyde | 3, 4, 5-trimethoxybenzaldehyde |
| 10 | p-hydroxybenzoic acid | p-methoxymethylbenzoate |
| 11 | isoeugenol | 3-[3, 4-dimethoxyphenyl]-2-propene |

EXAMPLE 12

This example illustrates the preparation of 3, 4, 5-trimethoxybenzaldehyde from syringaldehyde.

In a three-neck flask (capicity 100 ml) equipped with a mechanical stirrer and reflux condenser, 20 ml of dimethylformamide, 10.0 g (0.054 mol) of syringaldehyde and 5.00 g (0.036 mol) of anhydrous potassium carbonate were placed and the mixture was heated under a nitrogen atmosphere to 100° C. To this mixture was added 8.00 ml (0.094 mol) of dimethyl sulfite. The mixture was maintained at about 100° C. for eight hours and then cooled to 25° C. and quenched with 500 ml water. The mixture was extracted with 100 ml of methylene chloride. The extracts were washed with water and concentrated in vacuo to give 4.0 g of 3, 4, 5-trimethoxybenzaldehyde.

EXAMPLE 13

This example illustrates the preparation of p-acetamidoanisole from p-acetamidophenol.

To a three-necked 100 ml flask equipped for reflux and fitted with a mechanical stirrer was added 10 ml (0.12 mol) of diemthyl sulfite, 2.0 g (0.014 mol) of potassium carbonate, 10 ml dimethylformamide and 5.0 g (0.033 mol) of p-acetamidophenol. The mixture was heated to 100° C. for six hours then quenched while hot with 200 ml of water. The solution was made basic with dilute caustic and the organic materials were extracted into methylene chloride. The extracts were concentrated in vacuo to give 3.2 g of p-acetamidoanisole.

EXAMPLE 14

This example illustrates the preparation of veratraldehyde from photocatechualdehyde.

To a three-necked 100 ml flask equipped for reflux and fitted with a mechanical stirrer was added 10 ml of dimethylformamide, 1.0 g (0.0072 mol) of protocatechualdehyde 1.0 g (0.007 mol) of potassium carbonate, and 4.0 ml (0.047 mol) of dimethyl sulfite. The mixture was heated for four hours to 100° C. then quenched hot with 200 ml of water. The organic material was extracted into methylene chloride and the extracts were washed with 15 ml of 12% caustic solution, twice with 25 ml of water and then concentrated in vacuo to obtain 0.4 g of crude veratraldehyde.

Dimethyl sulfite was examined for mutagenicity by the Ames test. The Ames test is used to estimate the potential carcinogenicity of chemicals by measuring the number of bacteria which mutate in the presence of the compound being tested relative to the number which spontaneously mutate in the absence of the compound. The Ames test is more fully reported in B. N. Ames, J. McCann, E. Yamasaki, *Mutat. Res.*, 31, 347 (1975). The test results indicated that dimethyl sulfite is on the order of 500 to 100 times less mutagenic than the alkyl sulfonates which are generally conceded to be orders of magnitude less hazardous than dimethyl sulfate.

From the above, it is apparent that the process of the invention provides a simple but effective route for the preparation of phenolic ethers from phenols with the use of a substantially less hazardous alkylating agent.

I claim:

1. A process for the melt phase preparation of an alkylated phenolic ether comprising
   reacting in the absence of a solvent at a temperature of at least the melting point of the phenolic compound a phenolic carbonyl compound containing an unreacted phenolic hydroxy group with an alkyl sulfite of the formula $(RO)_2SO$ in which R is a one to four carbon alkyl group until an alkylated phenol is produced, said reaction occuring in one step and without the intermediate production of a phenolate.

2. The process of claim 1 in which the phenolic carbonyl compound is a monocyclic phenolic aldehyde.

3. The process of claim 2 in which the phenolic aldehyde is selected from the group consisting of vanillin and syringaldehyde.

4. The process of claim 1 in which the reaction takes place in the presence of a base catalyst.

5. The process of claim 1 in which R in the formula for the alkyl sulfite is a one to four carbon alkyl group.

6. The process of claim 5 in which the alkyl sulfite is dimethyl sulfite.

7. A process for the preparation of an alkylated phenolic ether comprising reacting in the absence of a protic solvent, and in the presence of a dipolar aprotic solvent and a weak base catalyst, a phenolic carbonyl compound containing an unreacted phenolic hydroxy group with an alkyl sulfite of the formula $(RO)_2SO$ in which R is a one to four carbon alkyl group until an alkylated phenol is produced, said reaction occuring in one step and without the intermediate production of a phenolate.

8. The process of claim 7 in which the solvent is selected from the group consisting of dimethylformamide, dimethylsulfoxide, dimethylacetamide, acetone and sulfolane.

9. The process of claim 8 in which the weak base is a carbonate salt selected from the group consisting of sodium, potassium, magnesium and calcium carbonate.